United States Patent [19]

Forguy et al.

[11] Patent Number: 5,183,915

[45] Date of Patent: Feb. 2, 1993

[54] CATALYST AND PROCESS FOR THE PRODUCTION OF 3-CYANO-3,5,5-TRIALKYLCYCLOHEXA-NONE

[75] Inventors: Christian Forguy, Devon, Pa.; Frederick J. Goetz, Wilmington, Del.; Edward L. Graeber, Spring City; Michael J. Lindstrom, Downington, both of Pa.

[73] Assignee: Elf Atochem North America, Inc., Philadelphia, Pa.

[21] Appl. No.: 846,364

[22] Filed: Mar. 5, 1992

[51] Int. Cl.⁵ .................. C07C 253/30; C07C 253/10
[52] U.S. Cl. .................................................. 558/341
[58] Field of Search ........................................ 558/341

[56] References Cited

U.S. PATENT DOCUMENTS

| | | | |
|---|---|---|---|
| 4,299,775 | 11/1981 | Dubreux | 558/341 |
| 5,011,968 | 4/1991 | Thunberg et al. | 558/341 |
| 5,091,554 | 2/1992 | Huthmacher et al. | 558/341 |

FOREIGN PATENT DOCUMENTS

| | | |
|---|---|---|
| 0425806 | 5/1991 | European Pat. Off. . |
| 57-116038 | 7/1982 | Japan . |
| 61-3315 | 2/1986 | Japan . |
| 1047920 | 11/1966 | United Kingdom . |

*Primary Examiner*—Joseph Paul Brust

[57] ABSTRACT

The production of 3-cyano-3,5,5-trialkylcyclohexanone from the reaction of 3,5,5-trialkylcyclohexenone and hydrocyanide at elevated temperature and in the presence of a catalytic amount of an onium cyanide, is disclosed herein.

15 Claims, No Drawings

CATALYST AND PROCESS FOR THE PRODUCTION OF 3-CYANO-3,5,5-TRIALKYLCYCLOHEXANONE

BACKGROUND OF THE INVENTION

This invention concerns the preparation of isophoronenitrile or close homologs thereof by reacting a 3,5,5-trialkylcyclohexen-1-one with hydrocyanide (HCN) in the presence of a catalytic amount of an onium cyanide with or without an aqueous reaction medium.

PRIOR ART

Processes for the preparation of 3-cyano-3,5,5-trimethylcyclohexanone from isophorone (3,5,5, trimethylcyclohexenone) and hydrocyanide (hydrocyanic acid) or alkali metal salts thereof employing various catalysts or catalyst systems are well known. The product isophoronenitrile is an intermediate for the production of isophoronediamine, a hardener for epoxy resins, or a monomer which may be used in the synthesis of polyurethane or polyamine resins.

Significant patent disclosures concerning this technology include U.S. Pat No. 4,299,775 of B. Dubreux, which concerns the preparation of 3-cyano-3,5,5-trimethylcyclohexanone from isophorone and a cyanide (alkali metal) in the presence of a phase-transfer agent e.g., quaternary ammonium or phosphonium salts (bromide). The process requires the presence of water in which the cyanide is dissolved, or a mixture of a water-immiscible organic solvent and water is used as the reaction medium.

Japanese Patent No. 61-33157 discloses the production of cyanoisophorone by reacting isophorone and hydrocyanide in the presence of a catalytic amount of a quaternary ammonium or phosphonium hydroxide. The reaction medium contains a specified amount of water which when distilled off results in a loss of product due to the formation of a isophorone-water azeotrope (85% isophorone - 15% H$_2$O). Furthermore, the catalyst is water-soluble and is removed by acid washing at the end of the process thereby generating waste water containing cyanides and increasing disposal costs.

U.S. Pat. No. 5,011,968 to Thunberg et al. discloses substantially the same process as reported in the above-mentioned Japanese patent with subsequent removal of the catalyst by thermal destruction and nitrogen sparging. However, the quaternary ammonium hydroxide generates by-products such as hydrocyanic acid polymer and hydroxyketone, with product yields not exceeding 85%.

STATEMENT OF THE INVENTION

This invention is a process for the preparation of 3-cyano-3,5,5-trialkylcyclohexanone by the reaction of 3,5,5-trialkylcyclohexen-1-one with hydrocyanide at elevated temperature in the presence of a catalytic amount of an onium cyanide.

DETAILED DESCRIPTION OF THE INVENTION

This invention concerns the high speed, high yield preparation of 3-cyano-3,5,5-trialkylcyclohexanone, preferably cyanoisophorone, by reacting hydrocyanide (HCN) with 3,5,5-trialkylcyclohexen-1-one where the alkyl group has from 1 to 4 carbon atoms, e.g., methyl, ethyl, propyl, isopropyl, butyl, isobutyl or a mixture of these groups. Methyl is the preferred alkyl group based on the greater commercial consumption of the product. The reaction is carried out at elevated temperature in the presence of a catalytic amount of an onium cyanide. The process requires no water or organic solvent, as in the prior art, but water will not effect the facile reaction.

The ratio of reactants used in the process ranges from about 1:3 moles of hydrocyanide for each mole of 3,5,5-trialkylcyclohexenone with a ratio of about 1 to 1 being preferred. The rate of addition of hydrocyanide to the reaction is less critical under the conditions of this invention than in prior processes since the reactivity of HCN in the presence of the onium cyanide catalyst is much greater than that observed with earlier used catalysts. The reaction could be accomplished in a length of time as short as 10 minutes. However, the reaction will usually proceed to completion in from about 0.3 to about 5 hours, preferably from 0.5 to 1.5 hours depending upon reaction temperature or exothermicity control in the commercial reactor.

The temperature of the reaction ranges from about 70 to about 140° C., preferably from 90° to 120° C. The pressure is generally ambient but can be supplemented by charging nitrogen or other inert gas to the reactor, if desired. The reaction pressure ranges from about 0.5 to about 1.5 bars, preferably 1 to 3 bars.

Commercial hydrocyanide is normally stabilized by the vendor with about 1% phosphoric acid, based on the weight of the HCN, to avoid spontaneous polymerization. Experiments performed with pure HCN (without a stabilizer) resulted in an undesirable loss of HCN (5-10%) through polymerization under the conditions of the process of this invention. Accordingly, when feeding HCN to the reactor containing 3,5,5-trialkylcyclohexenone, phosphoric acid is also preferably added in an amount sufficient to stabilize the hydrocyanide from polymerization. The phosphoric acid reacts with the catalyst to form HCN and a phosphorous salt of a quaternary onium moiety.

The solvents which are generally used in the prior art are not necessary in the process of this invention. No excess of 3,5,5-trialkylcyclohexenone needs to be used since the yield is nearly quantitative when employing stoichiometric amounts of the reactants. Nevertheless, an excess of 3,5,5-trialkylcyclohexenone is not detrimental to the yield and may permit better handling of the crude product.

The onium cyanide catalysts used for this invention preferably have the general formula:

R R'R''R''' Z Y where R—R''' are the same or different C$_1$- C$_{18}$ alkyl, C$_6$-C$_8$ cycloalkyl, C$_6$-C$_{10}$ aryl or C$_7$-C$_{18}$ aralkyl groups, Z is N, P or As and Y is cyanide. Examples of these catalysts are tetramethylammonium cyanide, tetraethylammonium cyanide, tetrabutylammonium cyanide, benzyltrimethylammonium cyanide, lauryltributylammonium cyanide, cyclohexyltrimethylammonium cyanide, tetramethylphosphonium cyanide, tetraethylphosphonium cyanide, dimethyldiethylphosphonium cyanide, methyltriisopropylphosphonium cyanide, tetrabenzylphosphonium cyanide, octyltriphenylphosphonium cyanide, dimethyldiphenylphosphonium cyanide, octadecyltripropylphosphonium cyanide, tetraethylarsonium cyanide, tetra p-tolylarsonium cyanide, methyltrioctylarsonium cyanide, tetramethylarsonium cyanide and tetraphenylarsonium cyanide. The more preferred catalysts for this invention, based on availability and ease of preparation, are the tetra $C_1$-$C_4$ alkylammonium cyanides, most preferably, tetraethylammonium cyanide.

Alternatively, the catalyst may be a sulfonium or isothiuronium cyanide including, for example, trimethylsulfonium cyanide, triethylsulfonium cyanide, tributylsulfonium cyanide, tridodecylsulfonium cyanide, tribenzylsulfonium cyanide, triphenylsulfonium cyanide, dimethylbutylsulfonium cyanide, dimethyl-o-ethylphenylsulfonium cyanide, dibenzylallylsulfonium cyanide, tetramethylenemethylsulfonium cyanide, S-methylisothiuronium cyanide, S-methylisothiuronium cyanide, S-butylisothiuronium cyanide, S-cyclohexylisothiuronium cyanide, N,N,N',N'-S-pentamethylisothiuronium cyanide, N-ethyl-S-propylisothiuronium cyanide, S-benzyl-isothiuonium cyanide, and the like.

The catalyst is used in an amount ranging from about 0.1 up to about 10 percent, preferably from about 0.5 to about 2.5 percent based on the weight of the 3,5,5-trialkylcyclohexenone in the reaction.

The onium catalyst is easily prepared by the reaction of about stoichiometric amounts of an onium halide, e.g., chloride or bromide, with an alkali or alkaline earth metal cyanide in water or an inexpensive solvent such as a lower alkanol, preferably methanol, and the water or solvent distilled off, unless the water will be used in practicing the reaction. In a preferred embodiment of this invention, the catalyst is formed in situ. i.e., in the reaction vessel for forming the cyanoisophorone, or its homolog, and the solvent or water removed before starting the reaction.

When using a quaternary onium cyanide catalyst, it is advantageously combined with a catalyst enhancing amount of an alkali or alkaline earth metal lower alkylate to effect increased catalyst activity and a sharp reduction in the amount of quaternary onium cyanide catalyst required to catalyze the reaction. In particular, 1 wt. % of sodium methylate combined with 1 wt. % tetraethylammonium cyanide was as effective as 2.5 wt. % of tetraethylammonium cyanide (based on the weight of isophorone in the reaction). The alkylates which are mixed with the quaternary onium cyanide contain from 1 to 4 carbon atoms and include, for example, sodium methylate, potassium methylate, calcium methylate, sodium ethylate, potassium butylate, calcium ethylate, and the like. The preferred alkylate is sodium methylate. The alkylate is used in an amount of from about 0.1 part up to about 2 parts by weight for each part by weight of quaternary onium cyanide, preferably from about 1 part to 1 part by weight.

The process of this invention provides a new means to produce 3-cyano-3,5,5-trialkylcyclohexanone from 3,5,5-trialkylcyclohexenone and hydrocyanide with space/time yield higher than previously known processes. The process yield is better ($>92\%$) than in prior processes.

An important aspect of the process of this invention is that it is easily performed in the absence of water in the reaction medium, thus avoiding losses in organic raw materials and eliminating waste water treatment. The absence of water in the reaction also permits more process temperature latitude.

The benefits of the invention are primarily due to use of the new catalyst in this reaction which provides high activity and the right basicity to permit the Michael addition of HCN on the 3,5,5-trialkylcyclohexenone without forming more than 2% of the prior art by-products (hydrocyanic acid polymer and hydroxyketone)

EXAMPLES

The following examples are reported to demonstrate the process of this invention and processes of the prior art for comparison. All of the experiments reported in the examples were performed using a reactor consisting of a 125 ml., 5-necked European flask mounted on an electric stirrer-heater. The necks were used, respectively, for sampling, reactant and catalyst delivery, thermal measurement, stirring and as an outlet to a condenser and scrubber. A tube inserted in the neck accommodating the magnetic stirrer, is used to supply nitrogen to increase pressure, or to produce a small vacuum, in the reactor, if desired.

EXAMPLE 1

Into a 125 ml flask as described above was placed 13.8 g of isophorone (0.1 mole) and 0.40 g of tetraethylammonium cyanide (0.0025 mole). The temperature was increased to 105° C., while stirring the mixture. Then 2.7 g (0.1 mole) of HCN was added to the reactor over a 15-minute feed-time period. The HCN addition lead to an increase of the temperature to 112° C. The solution was kept at 110° C. for one more hour with stirring and the composition of the reaction mixture was then analyzed by gas chromatography (GC) It showed 92.5% 3-cyano-3,5,5-trimethylcyclohexanone (IPN), 2% diisophorone (hydroxyketone), along with 4.2% isophorone (IPHO) as the main compounds in the mixture.

EXAMPLE 2

The experiment as described in Example 1 was repeated except that the solution was kept at 110° C. for only 10 more minutes. After a total reaction time of 25 minutes, a GC analysis showed that the reaction was completed. The composition of the reaction mixture was 94.8% IPN, 0.5% di-isophorone and 2.5% isophorone.

EXAMPLE 3

The experiment as described in Example 1 was again repeated except that 0.4 g of water was added along with the 13.8 (0.1 mole) of isophorone and 0.40 g (0.0025 mole) of tetraethylammonium cyanide. After reaching a temperature of 105° C., 2.7 g (0.1 mole) of HCN were added over a 3-hour period. The GC analysis showed 92.8% IPN, 2.9% di-isophorone and 2.6% isophorone.

EXAMPLE 4

Four experiments were carried out in the reactor of Example 1 by varying the reaction temperature and the feed time of HCN 2.7 g (0.1 mole) to a solution of 13.8 g (0.1 mole) of isophorone, 0.16 g (0.0010 mole) of tetraethylammonium cyanide and 0.05 g (0.0010 mole) of sodium methylate. The conditions and GC analyses are reported below.

| Run | Temperature (°C.) | HCN feed time (hr) | IPN (%) | IPHO (%) | di-IPHO (%) |
|---|---|---|---|---|---|
| 1 | 110 | 0.5 | 90.0 | 8.0 | 1.6 |
| 2 | 110 | 1.0 | 89.7 | 8.3 | 1.5 |
| 3 | 120 | 1.0 | 90.3 | 7.9 | 1.1 |

| Run | Temperature (°C.) | HCN feed time (hr) | IPN (%) | IPHO (%) | di-IPHO (%) |
|---|---|---|---|---|---|
| 4 | 140 | 0.5 | 73.2 | 21.2 | 0.6 |

EXAMPLE 5

Example 3 was repeated except that tetrabutylammonium cyanide 0.27 g (0.0010 mole) was used instead of tetraethylammonium cyanide. After a total reaction time of 55 minutes (15 minutes feed-time and 40 minutes at 110° C.), a GC analysis gave 82.9% IPN, 2.4% di-isophorone and 12.4% isophorone.

EXAMPLE 6

This example is provided to show that the catalyst can be easily prepared from inexpensive chemicals, directly in the reaction pot, before the hydrocyanation reaction.

Into the 125 ml reaction flask of Example 1 were placed 0.40 g (0.0025 mole) of tetraethylammonium chloride and 0.12 g (0.0025 mole) of sodium cyanide with 2 ml of methanol. The mixture was stirred 15 minutes at room temperature. Then, the mixture was brought to 85° C. and methanol was distilled off. 13.8 g (0.1 mole) of isophorone was introduced in the flask and the solution heated up to 110° C., before adding 2.7 g of HCN over a 15 minutes feed-time period. After 10 more minutes, the composition of the reaction mixture was determined by GC. It gave 85% IPN, 2.5% di-isophorone and 11.9% isophorone.

We claim:

1. A process for the preparation of 3-cyano-3,5,5-trialkylcyclohexanone by the reaction of 3,5,5-trialkylcyclohexenone having from 1 to 4 carbon atoms in each alkyl group with HCN in the absence of water and in the presence of a catalytic amount of a quaternary ammonium or quaternary phosphonim cyanide, and employing reaction conditions which will form 3-cyano-3,5,5-trialkylcyclohexanone.

2. The process of claim 1 wherein said 3,5,5-trialkylcyclohexenone is 3,5,5-trimethylcyclohexenone.

3. The process of claim 1 wherein said elevated temperature ranges from about 70° to about 140° c.

4. The process of claim 1 wherein the 3,5,5-trialkylcyclohexenone is reacted with hydrocyanide at a mole ratio of from about 1:1 to about 1:3.

5. The process of claim 1 wherein said quaternary ammonium or quaternary phosphonium cyanide is tetraalkylammonium cyanide or tetraalkylphosphonium cyanide.

6. The process of claim 5 wherein said cyanide is mixed with an alkali or alkaline earth metal alkylate having from 1 to 4 carbon atoms, in a catalyst enhancing amount.

7. The process of claim 6 wherein said alkylate is an alkali metal methylate in an amount of from about 0.1 part up to about 2 parts by weight for each part of said cyanide.

8. The process of claim 7 wherein said cyanide is tetraethylammonium cyanide.

9. A process for the preparation of 3-cyano-3,5,5-trimethylcyclohexanone by the reaction of 3,5,5-trimethylcyclohexenone with HCN in the absence of water at a mole ratio of from about 1:1 to about 1:3, at a temperature ranging from about 70° to about 140° C. in the presence of a catalytic amount of a tetraalkylammonium or a tetraalkylphosphonium cyanide having from 1 to 4 carbon atoms in each alkyl group.

10. The process of claim 9 wherein said tetraalkylammonium or tetraalkyl phosphonium cyanide is mixed with an alkali metal alkylate having from 1 to 4 carbon atoms in a catalyst enhancing amount.

11. The process of claim 10 wherein the catalyst is tetraethylammonium cyanide in an amount of from about 0.1 up to about 10% based on the weight of the 3,5,5-trimethylcyclohexenone, and said alkali metal alkylate is sodium methylate in an amount of from about 0.1 part up to about 2 parts by weight for each part of tetraethylammonium cyanide.

12. The process of claim 9 wherein said mole ratio is from about 1 to about 1, said temperature is from about 90° to 120° C., and the catalyst is tetraethylammonium cyanide in an amount of about 0.5 to about 2.5 percent based on the weight of said 3,5,5 trimethylcyclohexenone.

13. The process of claim 12 wherein said tetraethylammonium cyanide is mixed with sodium methylate in an amount of from about 1 part to about 1 part by weight.

14. The process of claim 9 wherein phosphoric acid is added to the reaction in an amount sufficient to stabilize hydrocyanide from polymerization.

15. The process of claim 12 wherein phosphoric acid is added to the reaction in an amount of about 1% based on the weight of said hydrocyanide.

* * * * *